Figure 1:
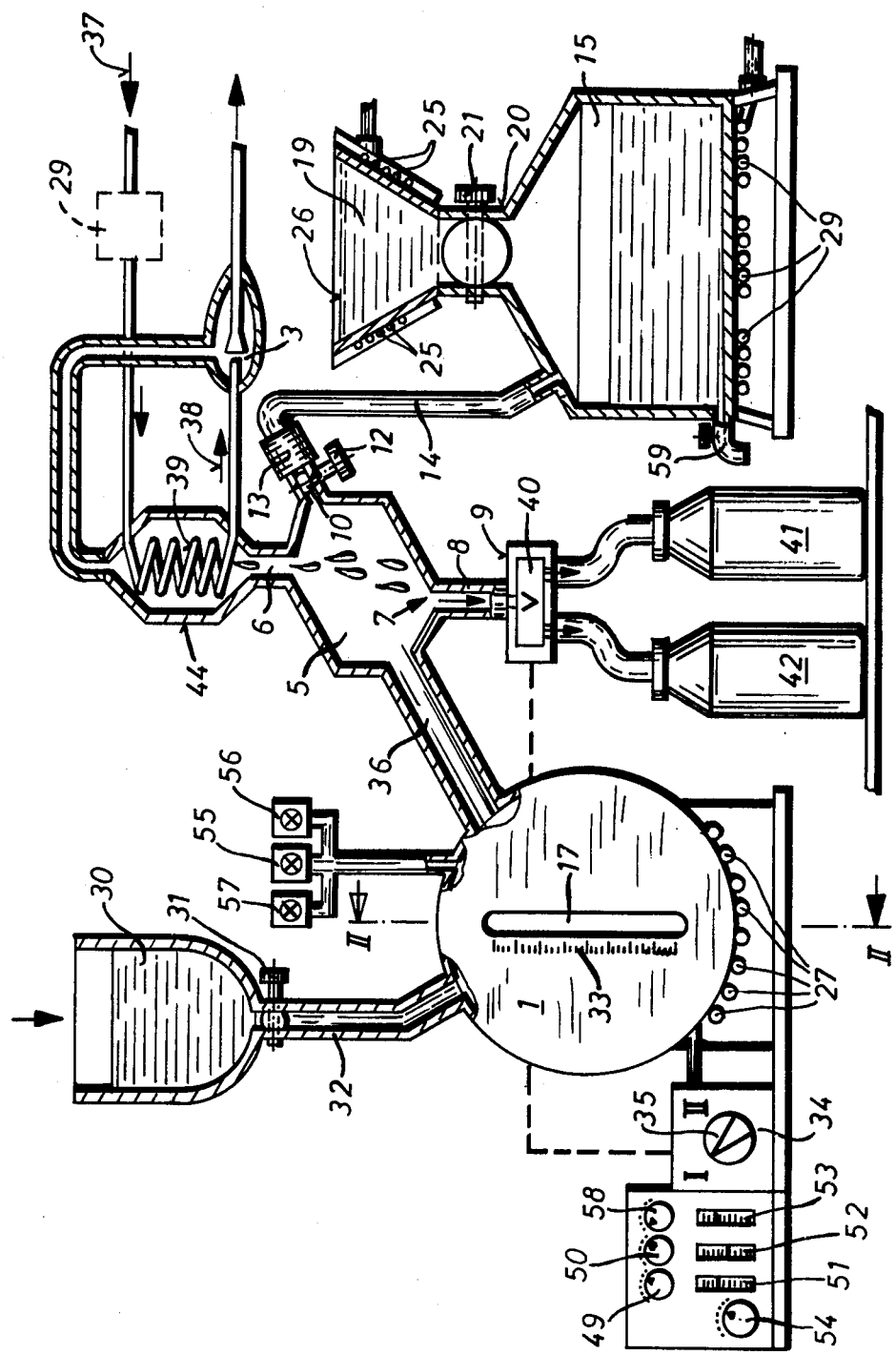

United States Patent [19]

Hamann

[11] 4,285,775
[45] Aug. 25, 1981

[54] APPARATUS FOR THE RECOVERY OF XYLENOL AND/OR PARAFFIN

[76] Inventor: Wolfgang Hamann, Felsenkellerweg 3,, D-6333 Braunfels, Fed. Rep. of Germany

[21] Appl. No.: 155,957

[22] Filed: Jun. 3, 1980

[51] Int. Cl.³ .............................................. B01D 3/02
[52] U.S. Cl. .................................. 202/160; 202/172; 202/178; 202/185 E; 202/197; 202/200; 202/205; 202/206; 202/235; 422/247
[58] Field of Search ................... 202/172, 178, 185 E, 202/189, 197, 200, 202, 205, 206, 232, 235, 160; 422/247

[56] References Cited

U.S. PATENT DOCUMENTS

| 20,760 | 6/1858 | Campbell | 202/186 |
|---|---|---|---|
| 643,131 | 2/1900 | Hempel | 202/235 |
| 1,346,537 | 7/1920 | Flowers | 202/200 |
| 2,975,107 | 3/1961 | Friedman | 202/172 |
| 3,156,533 | 11/1964 | Imber | 422/247 |
| 3,397,119 | 8/1968 | Bourland | 202/205 |

Primary Examiner—Frank Sever
Attorney, Agent, or Firm—Edmund M. Jaskiewicz

[57] ABSTRACT

A mixture of xylenol, water, alcohol and other substances is put into an evaporator tank which is adjusted to a pressure and temperature to evaporate the water and alcohol. The water and alcohol vapors flow through an expansion chamber into a condenser and the condensate flows back through a distributor and a control valve into a collector tank. Through a two-stage control dial a second temperature and pressure is imposed upon the evaporator tank to evaporate the xylenol which is similarly condensed and the condensate flows back through the distributor which control valve has been actuated to direct the xylenol into a second collector tank. A second evaporator is connected through a selectively operable shut-off valve to the expansion chamber. The second evaporator tank is provided with an inlet funnel which can be heated to melt solid paraffin therein. A filter is within this funnel to filter out solid foreign matter.

10 Claims, 2 Drawing Figures

APPARATUS FOR THE RECOVERY OF XYLENOL AND/OR PARAFFIN

The present invention relates to an apparatus for the recovery of xylenol and/or paraffin, more particularly, to the recovery of xylenol and paraffin for histological purposes from mixtures of water, alcohol, tissue and other substances.

In pathology, particularly during histological operations, xylenol is used as a solvent. After use, the xylenol is generally contaminated with water, alcohol, organic tissue particles and other solid foreign matter. The particles of organic tissue are generally embedded in paraffin so as to obtain sections thereof for microscopic examination.

In order to recover xylenol from such mixtures, the procedure generally followed was to distill the xylenol mixture, such as by a fractionated distillation. However, such a distillation is an expensive and time-consuming operation. For such distillation, rotary condensers were primarily used and these condensers were made mostly of glass. The handling of such rather fragile apparatus requires expert knowledge and constant care. In addition, any residues remaining in this apparatus were very difficult to remove and frequently the glass structure were broken when it was attempted to remove the residue. As a result, xylenol has been recovered only in very small quantities up to the present time and paraffin is not at all recovered in medical laboratories.

It is therefore the principal object of the present invention to provide a novel and improved apparatus for the recovery of xylenol in mixtures of water, alcohol, tissue or other substances and for the recovery of paraffin or similar substances mixed with xylenol and solids.

It is another object of the present invention to provide such an apparatus for the recovery of xylenol and/or paraffin in a very short time without the necessity of utilizing highly trained laboratory personnel and also which eliminates the breaking of glass.

It is an additional object to provide such an apparatus which can also recover paraffin and which will separate the paraffin from the xylenol.

According to one aspect of the present invention an apparatus for the recovery of xylenol mixed with water, alcohol, tissue or other substances, and for the recovery of paraffin and similar substances mixed with xylenol and solids may comprise a first evaporator tank for receiving a xylenol mixture and a second evaporator tank for receiving paraffin having solid matter therein. The second evaporator tank has a funnel wih a filter connected to its inlet and the funnel can be heated for melting solid paraffin. Means are further provided for selectively controlling the temperature and pressure in both of said evaporator tanks. A condenser is connected to both evaporator tanks to receive vapors therefrom and the second evaporator tank may be selectively connected to the condenser. Connected to the condenser is a distributor having a selectively operable control valve to receive condensate and first and second collector tanks are connected to the distributor. Means are further provided for selectively operating the distributor control valve to connect either one of said first and second collector tanks to the condenser through the distributor so that each of said collector tanks will receive selectively a predetermined condensate.

The temperature and pressure within the first evaporator tank is regulated by a two-stage switch so that at the first stage the water and alcohol evaporate and are collected in a collector tank. In the second stage the control valve of the distributor is operated and the xylenol evaporates and is collected in the other of the collector tanks. Any residue which accumulates in the evaporator tanks can be drained by opening of a discharge outlet, particularly after this tank has been filled with a cleaning compound used primarily for removal of the paraffin residue. It is not necessary to disassemble the apparatus for cleaning.

At the same time, the condenser may be used to separate the xylenol from the paraffin. The paraffin in its solid state is placed in a funnel for the second evaporator tank which can be heated to 60°–70° C. to melt the paraffin. A paper filter within the funnel retains portions of the organic tissues and other foreign matter. The pressure and the temperature of the second evaporator tank may be set such the xylenol evaporates and its vapors are then flowed into the condenser so that the condensed xylenol can then flow into a suitable collector tank.

Figure 2:
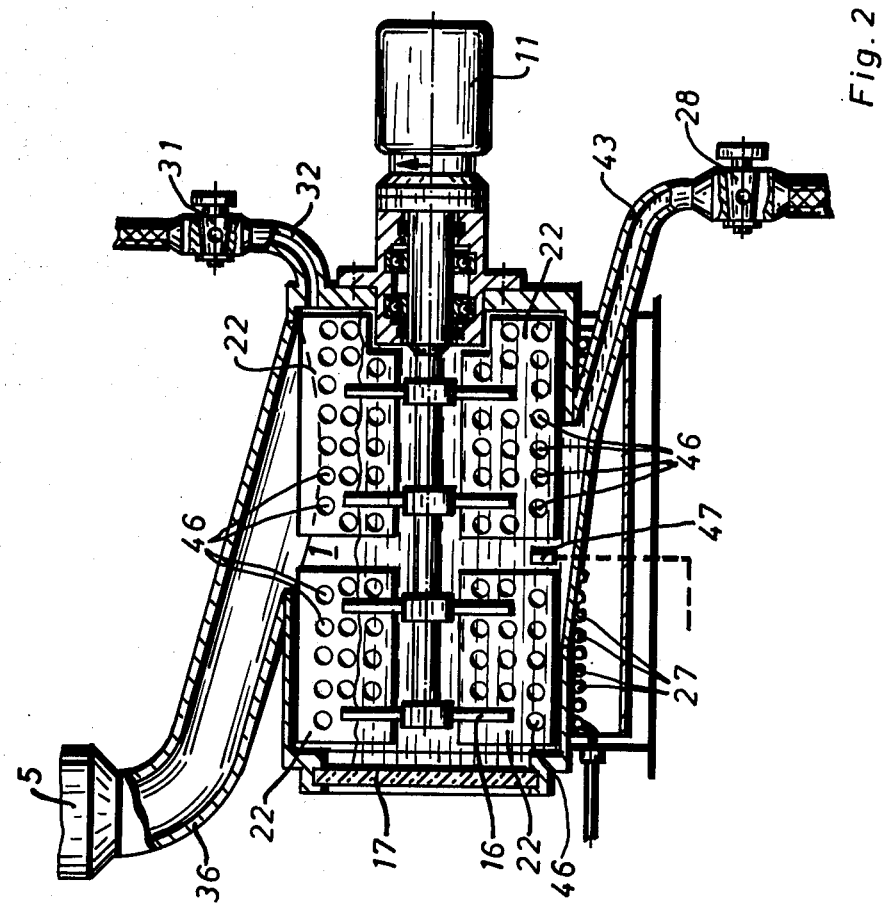

Other objects and advantages of the present invention will be apparent upon reference to the accompanying description when taken in conjunction with the following drawings, which are exemplary, wherein;

FIG. 1 is a schematic representation of the apparatus according to the present invention; and FIG. 2 is a sectional view taken along the line II—II of the FIG. 1.

Proceeding next to the drawings wherein like reference symbols indicate the same parts throughout the various views a specific embodiment and modifications of the present invention will be described in detail.

An open-ended container 30 which may be in the shape of a cone or funnel is provided to receive mixtures of xylenol and other substances such as water, alcohol, pieces of organic tissue and other foreign matter. The container 30 has a bottom opening to which is connected a shut-off valve 31 and an inlet pipe 32 which connects to an evaporator tank 1. A suitable filter which may be paper may be placed within the container 30 so as to retain pieces of foreign solid matter thereon.

The evaporator tank 1 is substantially cylindrical in shape and is shown in greater detail in FIG. 2. One end of the tank 1 is provided with a glass sight gauge 17 adjacent to which is positioned a scale of graduations 33 calibrated to indicate the quantity of the contents of tank 1.

Around the tank 1 or at least along its bottom surface there are provided heating coils or heating elements 27 to heat the contents of the tank. Within the tank 1 is an agitator 16 which is rotated around the central longitudinal axis of the tank by an electric motor 11. The agitator 16 has a number of vanes or paddles 22 with bores 46 therein. The outer edges of the vanes 22 are closely adjacent and almost in contact with the inner surface of the wall of the tank to ensure that the contents of the tank are in touch with the inner tank wall. The agitator 16 constantly stirs the xylenol mixture within the tank to increase heat transfer to the tank contents and thereby intensify the boiling process. This process is particularly intensified when the tank is provided with the heating elements surrounding the tank. Also, any retardation of the boiling process is thus eliminated.

A second evaporator tank 15 has short inlet opening 20 in which is positioned a shut-off valve 21 and the opening 20 is connected to a funnel 19 around which is a spiral heating coil 25 to heat the content to approximately 60°-70° C. In addition, a paper filter 26 is provided in the interior of the funnel 19 to filter out any solid foreign matter which may be in the solid paraffin which is placed in the funnel 19.

On the bottom surface of the evaporator tank 15 is a number of heating coils or units 29 so as to be able to heat the contents of the tank 15 to a maximum temperature of about 200° C. A discharge valve or drain tap 59 is provided in the bottom portion of the tank 15.

The evaporator tank 1 is connected by a pipe 36 to a vapor expansion chamber 5 and the evaporator tank 15 is connected to pipe 14, to a flexible sleeve 13, to an extension 10 on the vapor expansion chamber 5. A shut-off valve 12 is provided in the extension 10.

A condenser 44 is connected through a short length of pipe 6 to the upper portion of the expansion chamber 5. The condenser 44 is provided with a cooling coil 39 through which a cooling liquid such as tap water may be circulated in the directions indicated by the arrows 37 and 38. The cooling liquid may be further cooled or precooled by being flowed through a suitable aggregate 29'.

The water in the cooling coil 39 flows outwardly through a water jet pump 3 which is employed to produce a sub-atmospheric pressure in the apparatus.

In the bottom portion of the expansion chamber 5 there is provided a funnel-shaped opening 7 which is connected through a discharge pipe 8 to a distributor 9. The distributor 9 is provided with a magnetic control valve 40 which controls the flow of condensate into collector tanks 41 and 42. The connection pipe 8 may be provided with a sight glass or may be made entirely of a transparent material so that the condensate draining through the connection piece 8 may be observed.

The pressure and temperature in the evaporator tank 1 are regulated by means of an electrical control device 34 having a control switch or dial 35 which is moveable between two stages or positions designated as I and II. At the same time, the switch 35 actuates the magnetic control valve 40.

The tank 1 is provided with a temperature sensor 47 which indicates the temperature on dial 54 on the control device. The tank 1 is further provided with a drain pipe 43 and a shutoff valve 28 to drain out any tissue particles and other foreign matter which may be deposited in the bottom of the tank. After these residues have been discharged a new process can begin.

The control device is further provided with a rotatable control dial 49 to initially adjust the temperature in tank 1 at Stage I. The temperature at Stage II is adjustable by the rotatable dial 50. The pressure within tank 1 at Stage I is adjusted by the control indicator 51 and the pressure for Stage II by the control indicator 52. The actual temperature, as sensed in tank 1 by the control sensor 47 is shown on the dial indicator 54. The temperature can be regulated by control dial 58 and maximum overpressure is regulated by the scale control 53. The pressure control 52 is connected electrically with a pressure control valve 56, regulating valve 55 is provided to maintain the pressure in tank 1 constant. However, the valves 55 and 56 are so adjusted that in the event there is too great an underpressure or sub-atmospheric pressure, atmospheric air will flow into the tank 1 and into the condenser 44.

As a safety measure, a valve 57 is provided to function as an overpressure valve which opens automatically when the temperature climbs above 130° C., and thereby eliminates overpressure.

With this control device the temperatures and pressures can be selectively predetermined according to particular evaporation requirements of the substances to be evaporated.

In the operation of the above-described apparatus to recover xylenol, the contaminated xylenol or xylenol mixed with water, alcohol or other materials is placed into the container 30. By means of the shut-off valve 31 and pipeline 32 an amount of the xylenol mixture is introduced into the tank 1 to preferably half fill the tank as may be observed on the sight gauge 17. The motor 11 is started to rotate the agitator 16 and the heating elements 27 are energized to intensify the evaporatization process.

On the electrical control device 34, the dial switch 35 is set to Stage I which regulates the temperature in tank 1 to about 60° C. and the pressure in tank 1 to about 500 Torr (1 mm Hg). Before starting of the operation the temperature can further be regulated by the adjusting dial 49 and the pressure regulated by the control dial 51. The actual temperature in the tank is indicated on the dial 54. The pressure in the tank 1 can be held constant by the regulating valve 55.

The switching device 34 may also comprise thermostats, which are not shown, which maintain the temperature in the evaporator tank 1 constant.

In Stage I, the water and alcohol contained in the xylenol mixture will evaporate. The water and alcohol vapors are conveyed through pipe 36 into expansion chamber 5 and then into the condenser 44. The vapors are cooled by means of the cooling coil 39 and the condensate flows back over the connecting pipe 6 into the vapor expansion chamber 5. The condensate is gathered in the funnel-shaped opening 7 and flows through connector 8 into distributor 9. The magnetic valve 40 has been actuated by the control dial or switch 35 so as to direct the condensate into the container or collector 41 which receives the water and alcohol.

After the water and alcohol have been evaporated, the dial 35 is then set to Stage II such that the temperature is increased to about 110° C. and the pressure decreased to about 200 Torr. The pressure, during Stage II, can be regulated by means of the adjustable dial 52. The dial 52 is connected electrically with the control valve 56. Under these conditions the xylenol will evaporate and its vapors will similarly enter the condenser 44 through pipe 36 and the expansion chamber 5. When the dial 35 was moved to Stage II, the magnetic valve was actuated so that the xylenol condensate flows into the container 42.

Solid paraffin which has been contaminated or otherwise mixed with xylenol is placed in the funnel 19 which has been provided with a more or less coarse filter which may be a paper filter 26. The funnel is heated through the heating elements 25 to melt the paraffin and the melted paraffin together with the xylenol flows into the evaporator tank 15. Any coarse residue such as tissue particles and other solid foreign matter are retained on the paper filter 26.

The xylenol evaporates in the evaporator tank 15 at a temperature of about 110° C. and at a pressure of 200 Torr produced by the water jet pump 3. Subsequently, the xylenol vapors will pass through the pipe 14 into the expansion chamber 5 and then into the condenser 44. The condensate formed on the cooling coil 39 flows back through the connector 8 and distributor 9 into the collector tank 42.

In order to evaporate xylenol in the evaporator tank 15 the same temperatures and pressures are applied which are utilized during the evaporation process in evaporator tank 1.

Once the apparatus has been adjusted, only the dial 34 need be set at the desired Stage I or II for the recovery of the xylenol and paraffin.

It is therefore apparent that a principal advantage of the present invention resides in the reliable but simple apparatus which can be easily operated to permit the selective recovery of xylenol and paraffin wherein all foreign matter, such as tissue particles and the like, remain either in the first evaporator tank or in the filter of the second evaporator tank. Also, this foreign matter residue is easily removed from the tanks and cleaning of the tanks is a simple and relatively short process. This not only permits economic operation of the laboratory facilities but reduces the cost of the raw materials required.

It will be understood that this invention is susceptible to modification in order to adapt it to different usages and conditions and, accordingly, it is desired to comprehend such modifications within this invention as may fall within the scope of the appended claims.

What is claimed is:

1. An apparatus for the recovery of xylenol mixed with water, alcohol, tissue or other substances and for the recovery of paraffin and similar substances mixed with xylenol and solids comprising a first evaporator tank for receiving a xylenol mixture, a second evaporator tank having an inlet and a funnel with a filter connected to said inlet to receive paraffin having foreign matter therein, said funnel having means thereon for heating said funnel to melt solid paraffin therein, means for selectively controlling the temperature and pressure in said first and second evaporator tanks, a condenser connected to said first evaporator tank and selectively connected to said second evaporator tank to receive vapors from said evaporator tanks, a distributor having a selectively operable control valve connected to said condenser to receive condensate therefrom, first and second collector tanks connected to said distributor, means for selectively operating said control valve to connect one of said first and second collector tanks to said condenser through said distributor so that each of the collector tanks will receive selectively a predetermined condensate, and a control unit having a two-stage control dial, one of said stages adjusts the temperature and pressure in said first evaporator tank to evaporator water and alcohol and to open the control to one of said collector tanks, the second of said stages adjusts the temperature and pressure in said first evaporator tank to evaporate xylenol and to open the control valve to the other of said collector tanks.

2. An apparatus as claimed in claim 1 and further comprising a vacuum pump connected to said evaporator tanks and said condenser to produce a sub-atmospheric pressure therein.

3. An apparatus as claimed in claim 2 wherein said vacuum pump comprises a water jet pump supplied by water circulated through a cooling coil of said condenser.

4. An apparatus as claimed in claim 1 wherein said temperature and pressure controlling means further comprises a control valve to connect said evaporator tanks to the atmosphere.

5. An apparatus as claimed in claim 1 and comprising means for circulating a cooling liquid through a cooling coil of said condenser and aggregate means connected with said cooling means for cooling the liquid entering the cooling coil.

6. An apparatus as claimed in claim 1 and further comprising a vapor expansion chamber connected between said first evaporator tank and said condenser through which vapors from said first evaporator tank flow to said condenser, means for selectively connecting said expansion chamber to said second evaporator tank, said distributor being connected to said expansion chamber so that condensate from said condenser flows through said expansion chamber to the distributor.

7. An apparatus as claimed in claim 6 wherein at least one of said condenser and said expansion chamber has a transparent portion.

8. An apparatus as claimed in claim 6 wherein said connecting means comprises a first shut-off valve between said expansion chamber and said second evaporator tank and a second shut-off valve between said expansion chamber and said first evaporator tank.

9. An apparatus as claimed in claim 1 wherein said first and second evaporator tanks each has a selectively operable discharge opening in the bottom portions thereof to drain residue therefrom.

10. An apparatus as claimed in claim 1 and further comprising a container connected to an inlet of said first evaporator tank for receiving a xylenol mixture and a filter in said container.

* * * * *